(12) United States Patent
Smiley et al.

(10) Patent No.: US 8,257,942 B2
(45) Date of Patent: Sep. 4, 2012

(54) TISSUE EMBEDDING MATRIX

(75) Inventors: John F. Smiley, Congers, NY (US); Cynthia Bleiwas, Pamona, NY (US)

(73) Assignee: The Research Foundation For Mental Hygiene, Inc., Albany, NY (US)

( * ) Notice: Subject to any disclaimer, the term of this patent is extended or adjusted under 35 U.S.C. 154(b) by 1426 days.

(21) Appl. No.: 11/775,302

(22) Filed: Jul. 10, 2007

(65) Prior Publication Data

US 2008/0009028 A1 Jan. 10, 2008

Related U.S. Application Data

(60) Provisional application No. 60/806,806, filed on Jul. 10, 2006.

(51) Int. Cl.
*C12Q 1/02* (2006.01)
(52) U.S. Cl. ...................................................... 435/40.5
(58) Field of Classification Search ....... 435/40.5–40.52
See application file for complete search history.

*Primary Examiner* — Ralph Gitomer
*Assistant Examiner* — Robert Yamasaki
(74) *Attorney, Agent, or Firm* — David L. Nocilly; Bond Schoeneck & King

(57) ABSTRACT

The invention is a matrix for preparing a tissue sample made of saline, albumin, gelatin, formaldehyde, a detergent, sucrose, lysine, and glutaraldehyde. The matrix is formed by first preparing a solution of saline, albumin, and gelatin, and then mixing the solution with formaldehyde, a detergent, and sucrose. Immediately prior to fixation of the tissue, a separately prepared lysine-glutaraldehyde mixture is added. The resulting matrix will harden rapidly and may be used to fix tissue samples for histological processing. In particular, a layer of the matrix may be poured into a mold and allowed to harden to form a base. One or more tissue samples may then be pinned to the base of matrix in the mold and then covered with the matrix. Once the matrix hardens, the pins and mold may be removed, and the tissue sample or samples embedded in the matrix are ready for sectioning.

3 Claims, 4 Drawing Sheets

TISSUE EMBEDDING MATRIX

CROSS-REFERENCE TO RELATED APPLICATIONS

This application claims priority to U.S. Provisional Patent Application Ser. No. 60/806,806, filed Jul. 10, 2006.

BACKGROUND OF THE INVENTION

1. Field of the Invention

The present invention relates to tissue sample processing and, more specifically, to a matrix for embedding multiple tissue samples for histological processing.

2. Description of the Related Art

Suspending mediums, such as tissue embedding matrixes, are useful during the sectioning and histological processing of tissue samples, such as brain tissue. The tissue of interest is typically embedded in the matrix and then uniformly sectioned for further study, such as by a microscope. The matrix helps preserve and maintain the integrity, both structurally and chemically, of the one or more tissue samples prior to and during sectioning.

Currently available suspending media for histology are mainly one of two general types. One general type embeds tissue in a plastic or wax medium. A significant disadvantage of this approach is that the embedding process requires soaking the tissue in organic solvents that are harmful to the staining properties of the tissue. A second approach is to embed the tissue in a water-soluble matrix, for example using agarose or gelatin. This approach provides support for tissue during sectioning, but a disadvantage is that these water-soluble matrixes do not firmly adhere to the tissue sample after it is sectioned.

Matrices that firmly retain the tissue samples after they are sectioned are not widely available to researchers. A matrix that firmly retains tissue samples after sectioning allows researchers to simultaneously process corresponding sections from multiple tissue samples. This capacity for simultaneous processing insures that the corresponding tissue samples, retained in a single sheet of matrix, are processed as identically as possible, thus reducing experimental variability. Additionally, the retention of multiple tissue samples by a section of matrix substantially reduces the amount of labor involved in handling the sections during histological processing.

BRIEF SUMMARY OF THE INVENTION

It is a principal object and advantage of the present invention to provide a tissue embedding matrix that firmly retains samples after sectioning.

It is another object and advantage of the present invention to provide a tissue embedding matrix that minimally alters the histological staining properties of the tissue samples.

It is an additional object and advantage of the present invention to provide a tissue embedding matrix that is simple to prepare.

It is a further object and advantage of the present to provide a tissue embedding matrix that is easy to use.

Other objects and advantages of the present invention will in part be obvious, and in part appear hereinafter.

In accordance with the foregoing objects and advantages, the present invention is a matrix for embedding multiple tissue samples for histological processing that comprises a mixture of gelatin, saline, albumin, formaldehyde, a detergent, sucrose, and lysine-glutaraldehyde. The present invention is prepared by dissolving about 3.75 grams (0.5% of total solution) gelatin in 250 ml of a 0.9% saline solution at 60-70 degrees C. Next, 225 grams of albumin are stirred into 500 ml of a 0.9% saline solution. The 250 ml and 500 ml solutions are mixed, allowed to rest for about 4 hours, and then filtered. 100 ml of the 750 ml albumin/gelatin/saline solution is then mixed with 10 ml of 40% formaldehyde, 10 ml of 10% Triton X-100, and 50 grams of sucrose. Next, 100 ml of the albumin/formaldehyde solution is mixed with 5 ml of a 1:2 M lysine-glutaraldehyde solution. The mixture may then be poured over one or more tissue samples and allowed to harden.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

Figure 1:
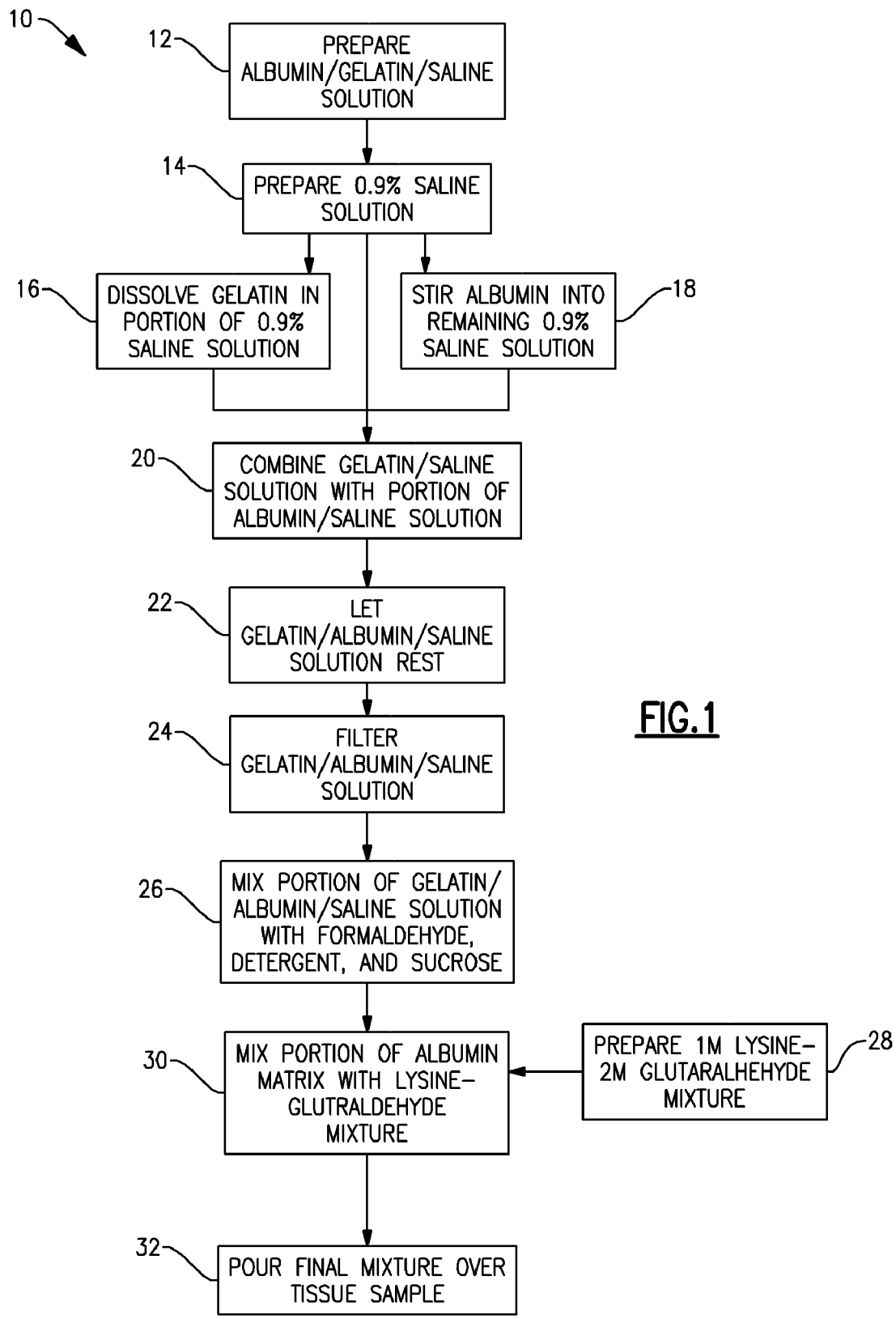
FIG. 1 is a flowchart of the method of preparing and using the tissue embedding matrix of the present invention.

Referring now to the drawings, wherein like reference numerals refer to like parts throughout, there is seen in FIG. 1 a method 10 for preparing a tissue embedding matrix according to the present invention. More particularly, formation of the matrix of the present invention begins with the preparation of an albumin/gelatin/saline solution 12 containing approximately 30% egg albumin, 0.5% gelatin, and 0.9% saline.

The albumin/gelatin/saline solution is formed by preparing 750 milliliters of a 0.9 percent saline solution 14. Next, 250 milliliters of the saline solution is heated to between 60-70 degrees Celsius, so that 3.75 grams of gelatin are then dissolved into the 250 milliliters of saline solution 16. Then 225 grams of albumin is slowly stirred into the remaining 500 milliliters of the 0.9% saline solution 18. The 250 ml gelatin/saline solution and the 500 ml albumin/saline solution are mixed together 20, allowed to rest for 4 hours 22, and then filtered 24.

The matrix of present invention also requires the preparation of a matrix solution 26 that is preferably prepared the day on which the tissue is to be embedded. The matrix solution 26 is prepared by mixing 100 milliliters of the filtered albumin/gelatin/saline solution with 10 milliliter of 40% formaldehyde, 10 milliliter of 10% Triton X-100 (a widely available non-ionic detergent), and 50 grams of sucrose. Other saccharides or, sugars may be used provided that they prevent freezing artifacts (e.g., ice) when the embedded tissue is frozen to be sectioned. It may be possible to omit the sugar altogether, and then soak the tissue fixed in the final matrix of the present invention soaked in sugar after embedding.

The matrix of present invention further requires the preparation of a lysine-glutaraldehyde mixture 28. The lysine-glutaraldehyde mixture is prepared by adding one part of 2.5 M L-lysine monohydrochloride to 1 part of 50 percent glutaraldehyde, thereby forming a ratio of 1M lysine to 2M glutaraldehyde. 2.5 M lysine comprises approximately 4.56 grams of lysine in 10 milliliters of solution. The L-lysine monohydrochloride may comprise AR grade L-lysine monohydrochloride, where FW equals 182.65, available from Sigma-Aldrich of St. Louis, Mo. Glutaraldehyde is preferably EM grade and should be kept refrigerated to prevent spoilage. L-Lysine-glutaraldehyde will first appear yellow, then orange, and then red as it hardens in about 3.5 minutes total.

The matrix of present invention may then be completed 30 by mixing approximately 100 milliliters of the matrix solution with between about 5 ml and about 7 ml of the 1:2 M lysine-glutaraldehyde solution 30 in the orange-colored state. The final matrix will begin to harden in just a few minutes, and should therefore be poured onto the tissue to be embedded 32 as soon as it is prepared. The use of about 7 ml of lysine-glutaraldehyde solution 30 gives a harder matrix that binds more tightly to the tissue sample. The use of about 5 ml lysine-glutaraldehyde solution 30 is preferred if cutting at 60-80 μm, and 7 ml is preferred if cutting thinner than 60 μm. When the final matrix hardens completely, approximately 15 minutes later, the matrix and tissue are ready to be cut. The final matrix is a fairly flexible gel with the consistency of soft rubber.

Figure 2:
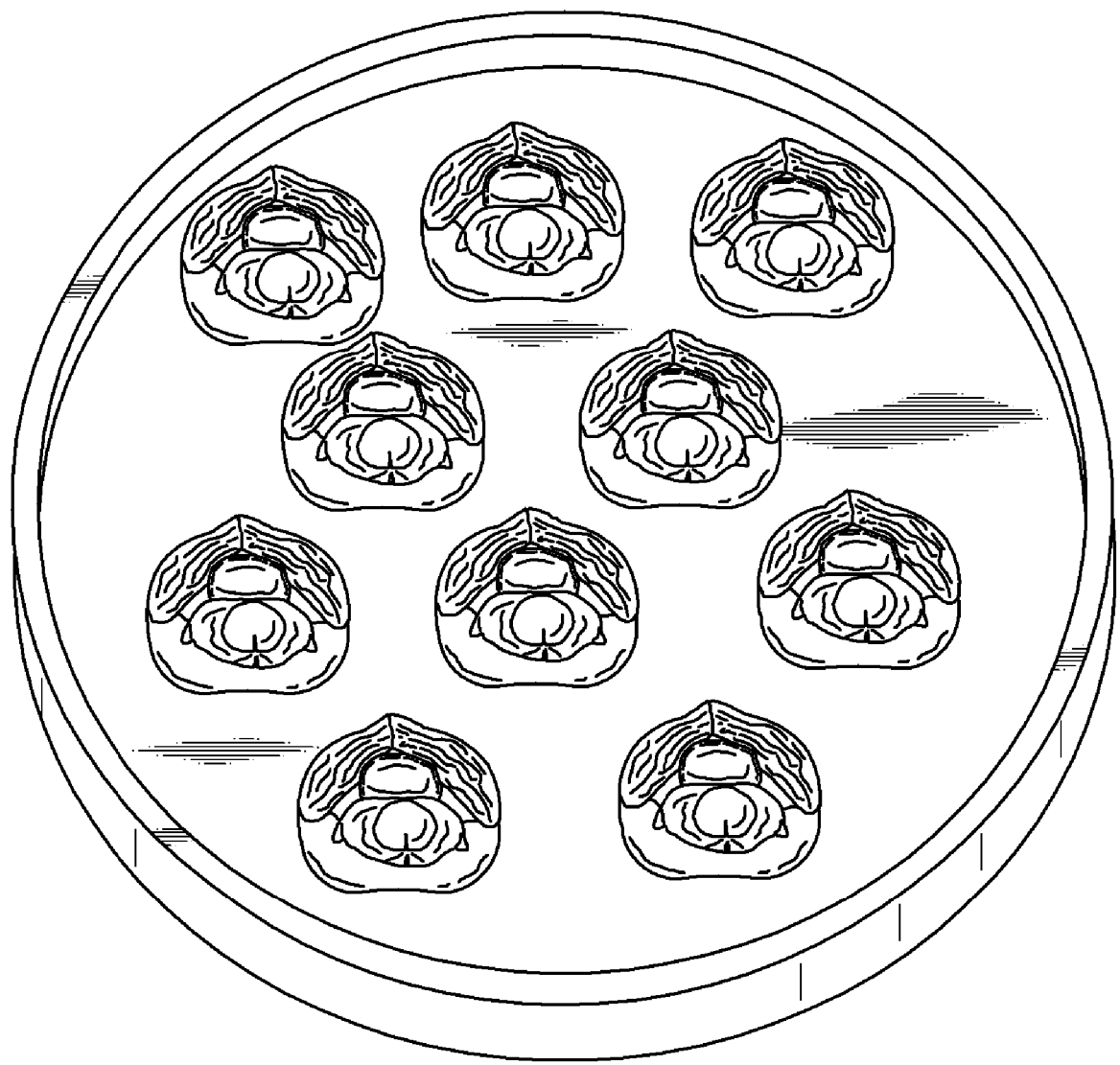
FIG. 2 is a photograph of multiple tissue samples pinned to a bed of the final matrix of the present invention in a mold in accordance with the present invention.

Multiple tissue samples can be embedded simultaneously in the matrix. A base of matrix approximately 1 cm thick is poured into a mold and allowed to harden. Referring to FIG. 2, multiple tissue samples, such as rat brains, may be secured to the hardened base, such as by using pins, with the tissue surface to be cut first facing downward. Securing the tissue is helpful for insuring that the tissue samples remain aligned until they are embedded in solidified matrix.

Figure 3:
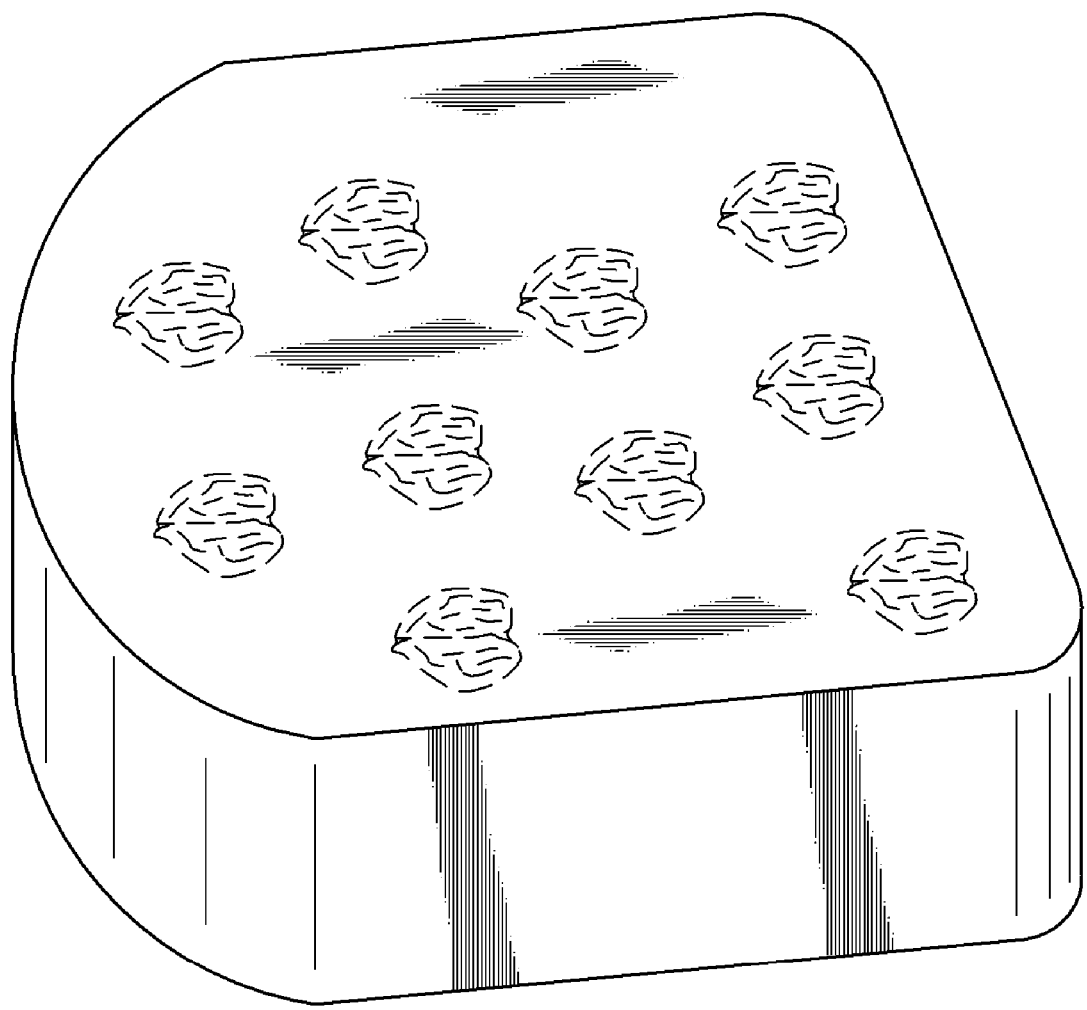
FIG. 3 is a photograph of multiple tissue samples embedded in the final matrix of the present invention and ready for sectioning.

Once tissue is positioned, the final matrix is poured into the mold around the tissue and allowed to harden. Once the final matrix hardens, the pins and mold may be removed, and the bottom layer of matrix peeled off to reveal the cutting surface. Referring to FIG. 3, multiple tissue samples are embedded in the final matrix and ready for sectioning.

Figure 4:
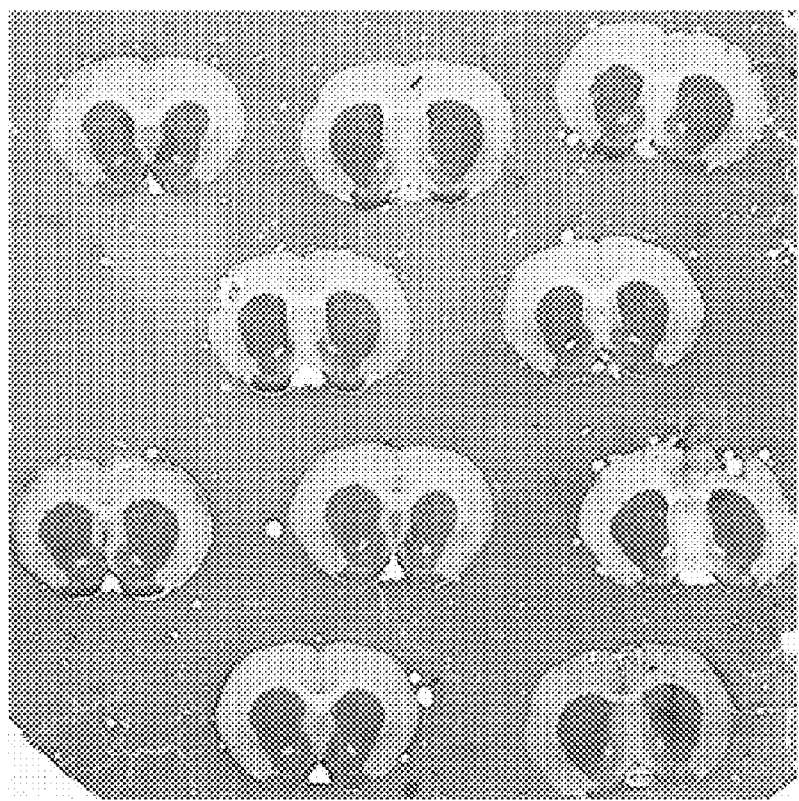
FIG. 4 is an immunochemical stain and cross-section of multiple tissue samples according to the present invention.
Figure 5:
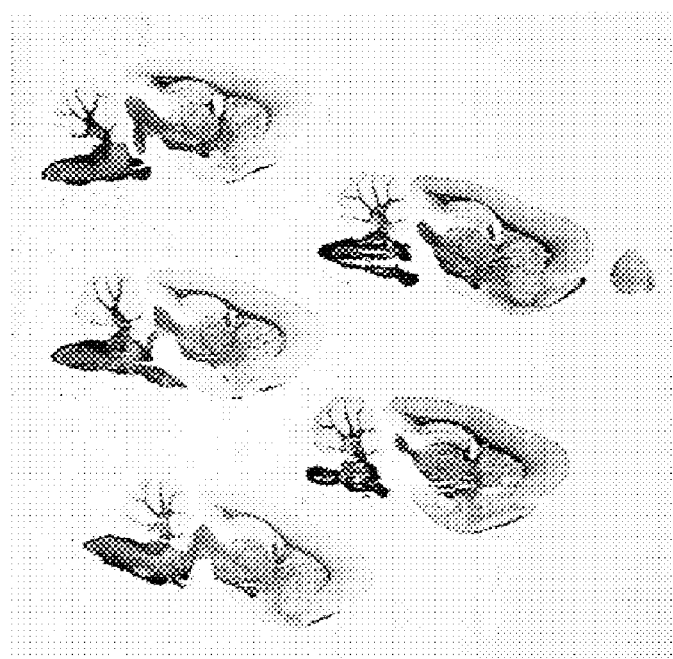
FIG. 5 is a histological stain and cross-section of multiple tissue samples according to the present invention.

The matrix of the present invention provides for surface cross-linking of the tissues to the matrix, even after sectioning, and preserves the tissue antigenicity, thereby allowing tissue, including multiple samples thereof, to be processed and cut as a single unit. There is seen in FIG. 4 multiple rat brain sections embedded in the matrix of the present invention and processed for immunocytochemical labeling. FIG. 5 depicts multiple rat brain sections embedded in the matrix of the present invention and then processed with a commonly used histochemical stain for myelin.

What is claimed is:

1. A matrix for preparing a tissue sample, comprising:
   between about 14.3 percent and 14.5 percent weight by volume of egg albumin;
   about 0.2 percent weight by volume of gelatin;
   about 0.4 percent weight by volume of NaCl;
   about 2.3 percent weight by volume of formaldehyde;
   about 0.6 percent weight by volume of a non-ionic detergent;
   between about 30.8 percent and about 31.4 percent weight by volume of sucrose;
   between about 1.1 percent and 1.5 percent weight by volume of lysine; and
   between about 1.2 percent and 1.6 percent weight by volume of glutaraldehyde.

2. The matrix of claim 1, wherein said lysine is L-lysine mono hydrochloride.

3. The matrix of claim 1, wherein said non-ionic detergent is polyethylene glycol p-(1,1,3,3-tetramethylbutyl)-phenyl ether

* * * * *

UNITED STATES PATENT AND TRADEMARK OFFICE
CERTIFICATE OF CORRECTION

| | | |
|---|---|---|
| PATENT NO. | : 8,257,942 B2 | Page 1 of 1 |
| APPLICATION NO. | : 11/775302 | |
| DATED | : September 4, 2012 | |
| INVENTOR(S) | : John F. Smiley and Cynthia Bleiwas | |

It is certified that error appears in the above-identified patent and that said Letters Patent is hereby corrected as shown below:

Col. 1, Line 7-9 should read

STATEMENT REGARDING FEDERALLY SPONSORED RESEARCH OR DEVELOPMENT

This invention was made with government support under grant number MH067138 awarded by the National Institutes of Health (NIH). The government has certain rights in the invention.

Signed and Sealed this
Twenty-ninth Day of January, 2013

David J. Kappos
*Director of the United States Patent and Trademark Office*